(12) United States Patent
Jung et al.

(10) Patent No.: US 8,202,488 B2
(45) Date of Patent: Jun. 19, 2012

(54) SYSTEM AND METHOD FOR REPOSITIONING A DIAGNOSTIC TEST STRIP AFTER INOCULATION

(75) Inventors: Sung-Kwon Jung, Granger, IN (US); Steven C. Charlton, Osceola, IN (US)

(73) Assignee: Bayer HealthCare LLC, New York, NY (US)

( * ) Notice: Subject to any disclaimer, the term of this patent is extended or adjusted under 35 U.S.C. 154(b) by 669 days.

(21) Appl. No.: 11/663,023

(22) PCT Filed: Sep. 19, 2005

(86) PCT No.: PCT/US2005/033297
§ 371 (c)(1),
(2), (4) Date: Feb. 21, 2008

(87) PCT Pub. No.: WO2006/034104
PCT Pub. Date: Mar. 30, 2006

(65) Prior Publication Data
US 2008/0257020 A1      Oct. 23, 2008

Related U.S. Application Data

(60) Provisional application No. 60/611,466, filed on Sep. 20, 2004.

(51) Int. Cl.
*G01N 33/00*   (2006.01)
(52) U.S. Cl. ...... 422/402; 422/58; 422/68.1; 422/82.01; 600/583; 600/584; 436/43; 436/44; 73/64.56
(58) Field of Classification Search ................... None
See application file for complete search history.

(56) References Cited

U.S. PATENT DOCUMENTS 5,109,866 A   5/1992   Guegan et al. ............... 128/771
5,510,266 A   4/1996   Bonner et al. .................. 436/43
(Continued)

FOREIGN PATENT DOCUMENTS

DE   101 56 811 A1   6/2003
EP   1 369 083 A1   12/2003
WO   WO 2005/085840 A1   9/2005

OTHER PUBLICATIONS

Written Opinion of the International Searching Authority corresponding to co-pending International Patent Application No. PCT/US2005/033297, European Patent Office, dated Jan. 19, 2006, 6 pages.

(Continued)

*Primary Examiner* — Sally Sakelaris
(74) *Attorney, Agent, or Firm* — Nixon Peabody LLP

(57) ABSTRACT

A system for analyzing the concentration of an analyte in a fluid sample comprises a test strip and a meter. The test strip is capable of being inoculated by the fluid sample. The test strip includes a test element, which contains at least one reagent adapted to cause a reaction when brought into contact with the analyte. The meter includes a read-head, a repositioning device, and a display. The read-head is capable of producing a signal indicative of the reaction between the analyte and the at least one reagent. The display being capable of displaying the analyte concentration. The repositioning device is adapted to move the test strip from a loading position to a testing position. The testing position positions the test element proximate to the read-head.

33 Claims, 4 Drawing Sheets

U.S. PATENT DOCUMENTS

| | | | |
|---|---|---|---|
| 5,810,199 A | 9/1998 | Charlton et al. | 221/31 |
| 2001/0027277 A1* | 10/2001 | Klitmose | 600/583 |
| 2002/0057993 A1* | 5/2002 | Maisey et al. | 422/82.01 |
| 2002/0188224 A1 | 12/2002 | Roe et al. | 600/584 |
| 2003/0212344 A1* | 11/2003 | Yuzhakov et al. | 600/583 |
| 2005/0163661 A1* | 7/2005 | Ziegler | 422/68.1 |

OTHER PUBLICATIONS

International Search Report corresponding to co-pending International Patent Application No. PCT/US2005/033297, European Patent Office, dated Jan. 19, 2006, 5 pages.

* cited by examiner

SYSTEM AND METHOD FOR REPOSITIONING A DIAGNOSTIC TEST STRIP AFTER INOCULATION

CROSS-REFERENCE TO RELATED APPLICATION

This application claims priority to U.S. Provisional Application No. 60/611,466, filed on Sep. 20, 2004.

FIELD OF THE INVENTION

The present invention relates generally to diagnostic instruments and, more particularly, to a system and method for repositioning a diagnostic test strip after inoculation for use in determining the concentration of an analyte in a liquid sample.

BACKGROUND OF THE INVENTION

Test strips (e.g., biosensors) containing reagents are often used in assays for determining the analyte concentration in a fluid sample. The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. Each test requires that a new test sensor be used and, thus, cost of the individual test sensors is important to the users.

The material costs for an individual test strip (and the packing costs associated therewith) increase as the size of the individual test strips increase. Therefore, to minimize the cost of the test sensors, it is desirable to make the test strips as small as possible. However, as the size of the test sensors decreases, generally the difficulty in handling and manipulating the strip by a user increases. Additionally, the risk of contaminating a read-head on a meter increases as the size of the test strip decreases.

Therefore, it would be desirable to have a system and method that uses a diagnostic test strip and addresses these issues.

SUMMARY OF THE INVENTION

A system for analyzing the concentration of an analyte in a fluid sample is disclosed according to one embodiment of the present invention. The system includes a test strip and a meter. The test strip is capable of being inoculated by the fluid sample. The test strip includes a test element, the test element contains at least one reagent adapted to cause a reaction when brought into contact with the analyte in the fluid sample. The meter includes a read-head, a repositioning device, and a display. The read-head is capable of producing a signal indicative of the reaction between the analyte and the at least one reagent. The display is capable of displaying the concentration of the analyte. The repositioning device is adapted to move the test strip from a loading position to a testing position, the testing position positioning the test element proximate to the read-head.

A meter for repositioning a test strip and determining the concentration of an analyte in a fluid sample is disclosed according to one embodiment of the present invention. The meter includes a read-head and a repositioning device. The read-head is capable of producing a signal indicative of a reaction between the analyte and at least one reagent. The repositioning device includes a test-strip-seating device and is adapted to move the seated test strip from a loading position to a testing position. The testing position positions a test element on the seated test strip proximate to the read-head. The meter is adapted to maneuver the seated test strip when the meter is manipulated.

A method for analyzing the concentration of an analyte in a fluid sample is disclosed according to one embodiment of the present invention. The method includes the act of providing a meter including a read-head and a repositioning device. The repositioning device including a seating device located thereon. The method further includes the act of providing a test strip having a test element and an end portion removed spatially from the test element. The end portion of the test strip is adapted to correspond to the seating device. The method further includes the act of seating the test strip onto the corresponding seating device. The method further includes the act of inoculating the test element with the fluid sample. The fluid sample contains the analyte to be analyzed. The method further includes the act of repositioning the test strip, after inoculating the test element. The repositioning brings the test element proximate to the read-head via the repositioning device. The method further includes the act of determining the analyte concentration in the fluid sample.

The above summary of the present invention is not intended to represent each embodiment, or every aspect, of the present invention. Additional features and benefits of the present invention are apparent from the detailed description, figures, and claims set forth below.

DESCRIPTION OF ILLUSTRATED EMBODIMENTS

The present invention is directed to a meter that contains a repositioning device for seating, holding, and repositioning a test strip. The meter and test strip are used to determine concentrations of at least one analyte. Analytes that may be measured using the present invention include glucose, lipid profiles (e.g., cholesterol, triglycerides, LDL and HDL), microalbumin, hemoglobin AIC, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, other body fluids like ISF (interstitial fluid) and urine, or other (non-body) fluid samples.

Figure 1:
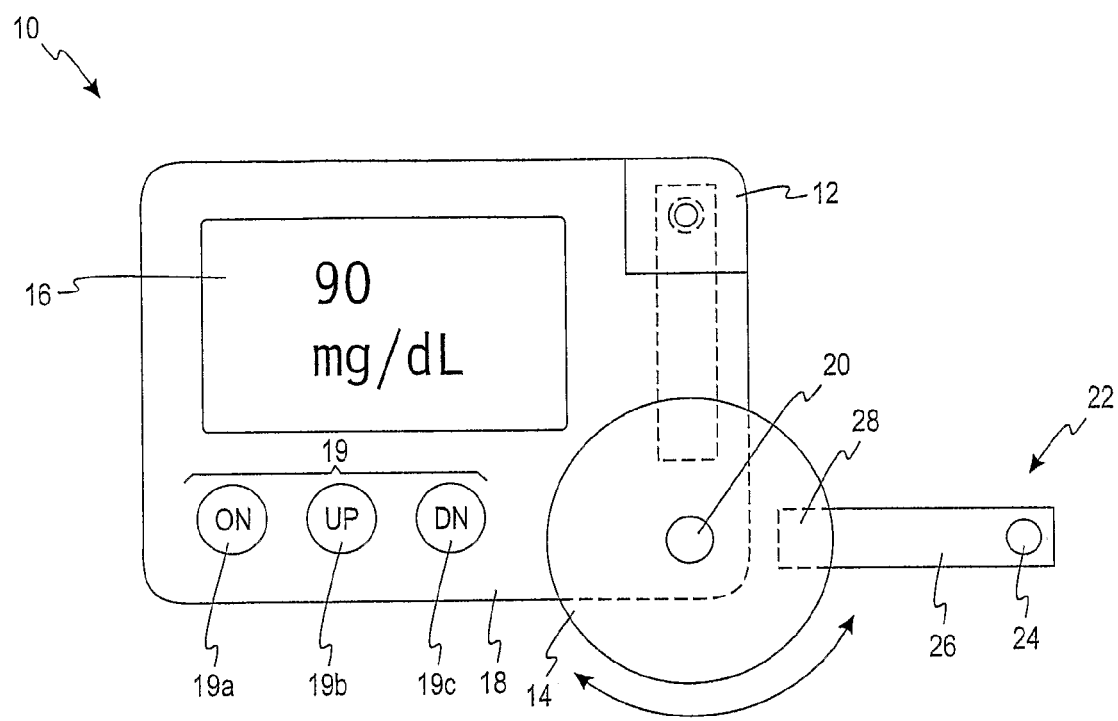
FIG. 1 is a top view of a meter and test strip according to one embodiment of the present invention.

Turning now to the drawings and initially to FIG. 1, a meter 10 is illustrated according to one embodiment of the present invention. The meter 10 includes a read-head 12, a repositioning device 14, and a display 16 located on a face 18 of the meter 10. The read-head 12 may be an optical read-head that can be used to determine the analyte content in a fluid sample according to one embodiment. Typically, an optical read-head includes, for example, a light-emitting diode (LED) and a phototransistor.

Figure 2:
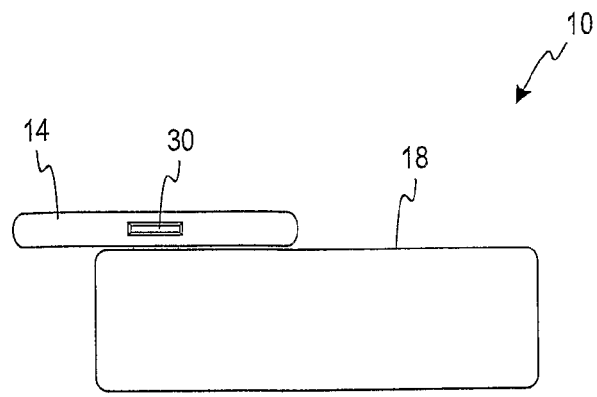
FIG. 2 is a side view of the meter of FIG. 1 and a repositioning device.

The repositioning device 14 of FIG. 1 is a wheel that is attached to the meter 10 with a pin 20. The repositioning device 14 contains a seating device for seating a corresponding test strip 22 on the repositioning device 14. According to one embodiment, the seating device is a pocket 30 that corresponds to an end portion 28 of the test strip 22, as described in greater detail below with respect to FIG. 2. The pocket 30 is adapted to allow a user to insert a test strip 22 therein.

The repositioning device 14 is designed to pivot about an axis when a test strip 22 has been seated thereon. The repositioning device 14 is adapted to rotate at least approximately 90°, according to one embodiment of the present invention. In one embodiment of the present invention, the repositioning device 14 is adapted to rotate at least a full 360° in both directions. In other embodiments, the repositioning device 14 is adapted to rotate at least approximately 45°. In yet other embodiments of the present invention, the repositioning device 14 is adapted to rotate between approximately 90° and 180°. Additionally, in other embodiments of the present invention, the repositioning device 14 is adapted to reposition a test strip by other means, and should not be limited to merely rotating the repositioning device 14.

The test strip 22 includes a test element 24 located on a face 26 of the test strip 22. According to one embodiment, the test strip 22 is fashioned from an optically clear material, such as, for example, optically clear polyethylene terephthalate (PET). The test element 24 contains at least one reagents for reacting with an analyte of interest in a fluid sample. It is contemplated that two or more reagents may be included in the test element. The specific reagents incorporated into the test element 24 is a function of the analyte of interest and the type of read-head 12 to be used for determining the concentration of the analyte. For embodiments where the read-head 12 is an optical read-head, the reagents produce a colorimetric reaction indicative of the analyte concentration in the fluid sample.

In one embodiment of the present invention, for example, the reaction area could contain reagents adapted to the determination of glucose, such as the enzyme glucose oxidase in combination with indicators such as tetramethylbenzidine or dianisidine or 4-aminoantipyrine plus p-hydroxybenzenesulfonate in the presence of peroxidase. In another embodiment of the present invention, the enzyme glucose dehydrogenase could be used in combination with tetrazolium indicators such as p-iodonitrotetrazolium violet (INT), nitroblue tetrazolium (NBT) or tetranitroblue tetrazolium (TNBT), for example.

In yet another embodiment of the present invention where the analyte is cholesterol, the reagent area contains the enzymes cholesterol ester hydrolase and cholesterol oxidase plus indicators such as tetramethylbenzidine or dianisidine or 4-aminoantipyrine plus p-hydroxybenzenesulfonate in the presence of peroxidase.

In another embodiment of the present invention where the analytes are tryglycerides, the enzymes lipase, glycerokinase, glycerolphosphate dehydrogenase and diaphorase in combination with tetrazolium indicators such as p-iodonitrotetrazolium violet (INT), nitroblue tetrazolium (NBT) or tetranitroblue tetrazolium (TNBT) will produce a color indicative of the tryglyceride levels. In yet another embodiment of the present invention, the enzymes lipase, glycerokinase, glycerol phosphate oxidase combined with indicators such as tetramethylbenzidine or dianisidine or 4-aminoantipyrine plus p-hydroxybenzenesulfonate in the presence of peroxidase will produce color in response to triglycerides.

According to another embodiment of the present invention, where the analyte is the enzyme amylase, the reagent area contains, for example, the enzyme alpha glucosidase and the chromogenic indicator 4,6-ethylidene (G7) nitrophenyl (G1)-(alpha)D-maltoheptoside. In another embodiment of the present invention, hemoglobin can be detected using, for example, potassium ferricyanide, potassium cyanide and sodium bicarbonate.

Upon applying the sample to the test element 24, the analyte reacts with the at least one reagent located on the test element 24. The reaction is indicative of the analyte concentration in the sample and is evaluated using the read-head 12.

The test element 24 is adapted to be placed into contact with the fluid sample (e.g., a whole blood sample) to be tested. The whole blood sample may be generated by a lancing device such as a lancet. The whole blood sample may be obtained by a lancet that may be separate from the meter or may be integrated within the meter. The lancing device may obtain blood by, for example, pricking a person's finger.

The test strips 22 may be provided with a capillary channel that extends from the front or testing end of the sensors to the reagent material disposed on the test element 24. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that a color change occurs indicative of the analyte concentration in the blood being tested.

The display 16 may be a liquid crystal display or other suitable display for presenting information to a user. Some of the information that may be presented on the display 16 of the meter 10 include the following: an analyte mode indicator (to display the particular analyte to be tested), a battery indication, a numerical display, a temperature indication, or various combinations thereof. The display 16 may also present a glucose trend for the week to a user or any other desired type of information. The display 16 is also used to present the analyte concentration to a user once a test has been performed.

The meter 10 of FIG. 1 also includes a button set 19 that comprises several individual buttons 19a, b, c that are depressed to operate the electronics of the meter 10. The button set 19 may be used, for example, to recall and have presented on the display 16 the results of prior testing procedures. The button set 19 may also be used to set and display date and time information, and to activate reminder alarms that remind the user to conduct, for example, a blood glucose test according to a predetermined schedule. The button set 19 may also be used to activate certain calibration procedures for the meter 10 and read-head 12.

The meter 10 may also contain an opening for a battery-tray assembly. The battery-tray assembly includes a battery-tray in which a battery is disposed. The battery-tray assembly may be inserted into the opening in a side of the meter 10, in one embodiment. When so inserted, the battery provides power for the electronics within the meter 10, including the circuitry on the circuit board assembly (not shown), the read-head 12, and the display 16.

The repositioning device 14—as illustrated in FIG. 1—is in its loading and inoculation position. An end portion 28 is illustrated after having been inserted into the pocket 30 (see also FIG. 2) of the repositioning device 14. Once the end portion 28 has been inserted into the pocket 30, a user can inoculate the test element 24 by applying a fluid to the test element 24. Once the test element 24 has been inoculated, the repositioning device 14 is rotated to position the test element 24 so that the sample can be analyzed by the read-head 12. This position, shown in shadow in FIG. 1, is the testing position, according to one embodiment.

The repositioning device 14 helps to protect the read-head 12 from being contaminated by providing a mechanism for the test element 24 to be inoculated away from the read-head 12 and then repositioned once the sample has been applied. This is a particularly helpful feature as the size of the test strip 22 and test element 24 decrease.

The repositioning device 14 and the meter 10 also allow a user to handle, manipulate, and inoculate the test strip 22 even when the size of the test strip 22 decreases. Once the test strip 22 has been inserted into the pocket 30, a user can manipulate the test strip 22 by handling the meter 10 itself, without handling the test strip 22 directly. Thus, the size of the test strip 22 does not effect a user's ability to manipulate the test strip 22.

It should be noted that the test strip 22 may be a top-load strip, a semi-capillary strip, a capillary strip, etc. The types of test strips are well-known within the art and need not be described in further detail to understand the present invention. However, the present invention allows the size of these common test strips to be reduced, without detracting from their intended functionality.

An example of a typically sized test strip is 0.8×5 cm, while an example of a test strip of decreased size, may be, for example, 0.4×4 cm. Another example of a test strip of decreased size, for example, is 0.2×3 cm. However, it is contemplated that other sized test strips may be used in to perform the present invention.

Referring again to FIG. 2, the pocket 30 is illustrated according to one embodiment. The pocket 30 is adapted to seat the end portion 28 of the corresponding test strip 22 when the end portion 28 of the test strip 22 has been inserted therein. The pocket is designed such that the test strip 22 remains seated even when the repositioning device 14 is moved from the loading and inoculation position to the testing position.

Figure 3:
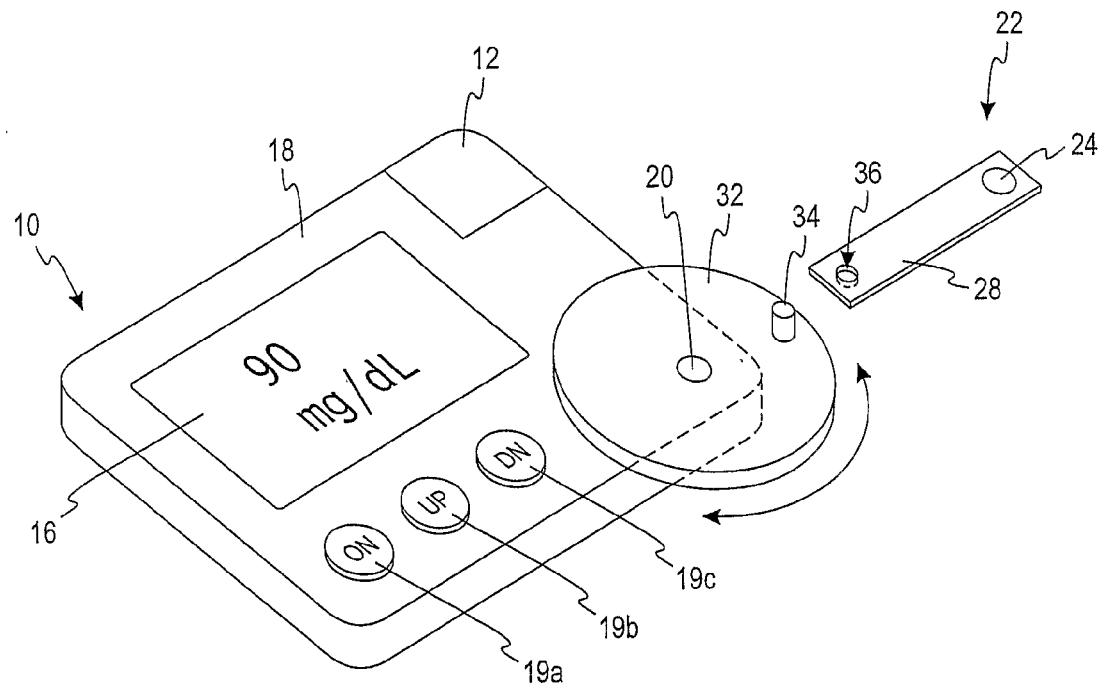
FIG. 3 is a perspective view of a meter, repositioning device, and test strip according to one embodiment of the present invention.

Referring now to FIG. 3, a repositioning device 32 is shown according to one embodiment of the present invention. The repositioning device 32 contains a post 34 adapted to seat the corresponding test strip 22 containing an aperture 36 through the end portion 28. In use, the post 34 is inserted through the aperture 36 in the end portion 28 of the test strip 22 while the repositioning device 14 is located in its loading and inoculation position.

Figure 4:
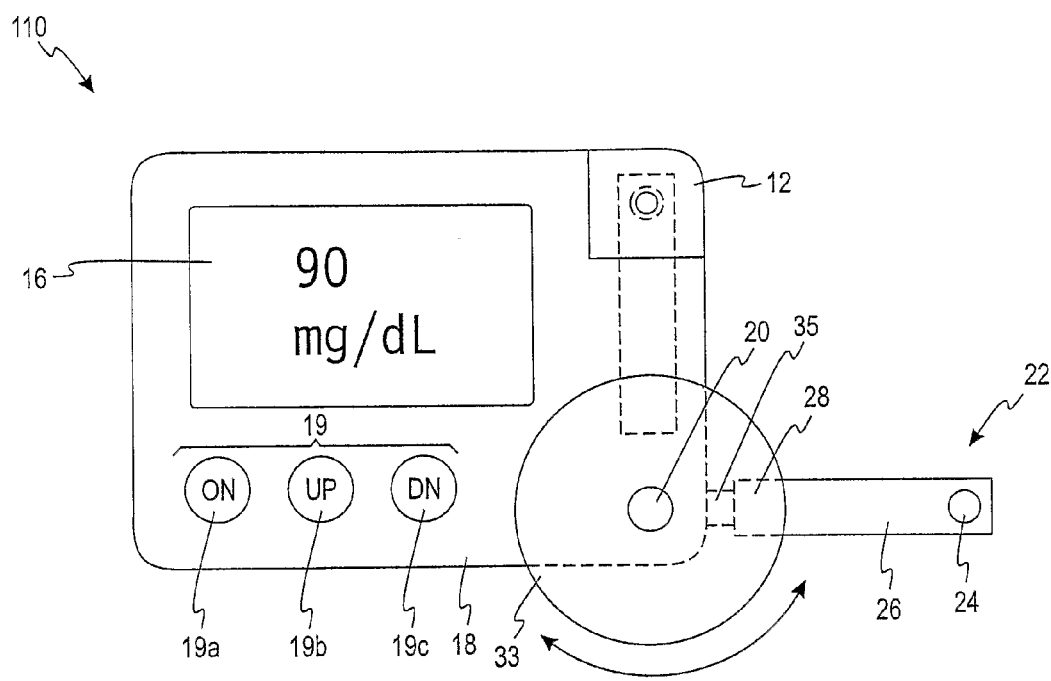
FIG. 4 is a top view of a meter and test strip according to a further embodiment of the present invention.

Referring to FIG. 4, a repositioning device 33 is shown according to a further embodiment of the present invention. The repositioning device 33 is a wheel that is attached to meter 110 with, for example, the pin 20. The repositioning device 33 contains a seating device for seating a corresponding test strip 22 on the repositioning device, which is described in more detail above in connection with FIGS. 1 and 2. Unlike FIGS. 1 and 2, the repositioning device 33 is adapted to automatically move from the loading position to the test position after a test strip 22 is inserted therein. In one embodiment, the repositioning device 33 is adapted to automatically rotate.

To assist in detecting the insertion of a test strip 22, a detector 35 is located on the repositioning device 33 in this embodiment. It is contemplated that other mechanisms may be used to detect the insertion of a test strip 22. After the detector 35 detects the presence of a test strip 22, the repositioning device 33 automatically moves to the read-head 12. The repositioning device 33 may be automatically rotated in various degrees such as those described above in repositioning device 14. Additionally, in other embodiments, a repositioning device may be adapted to automatically reposition a test strip by other methods and is not limited to rotating the repositioning device 33.

Figure 5:
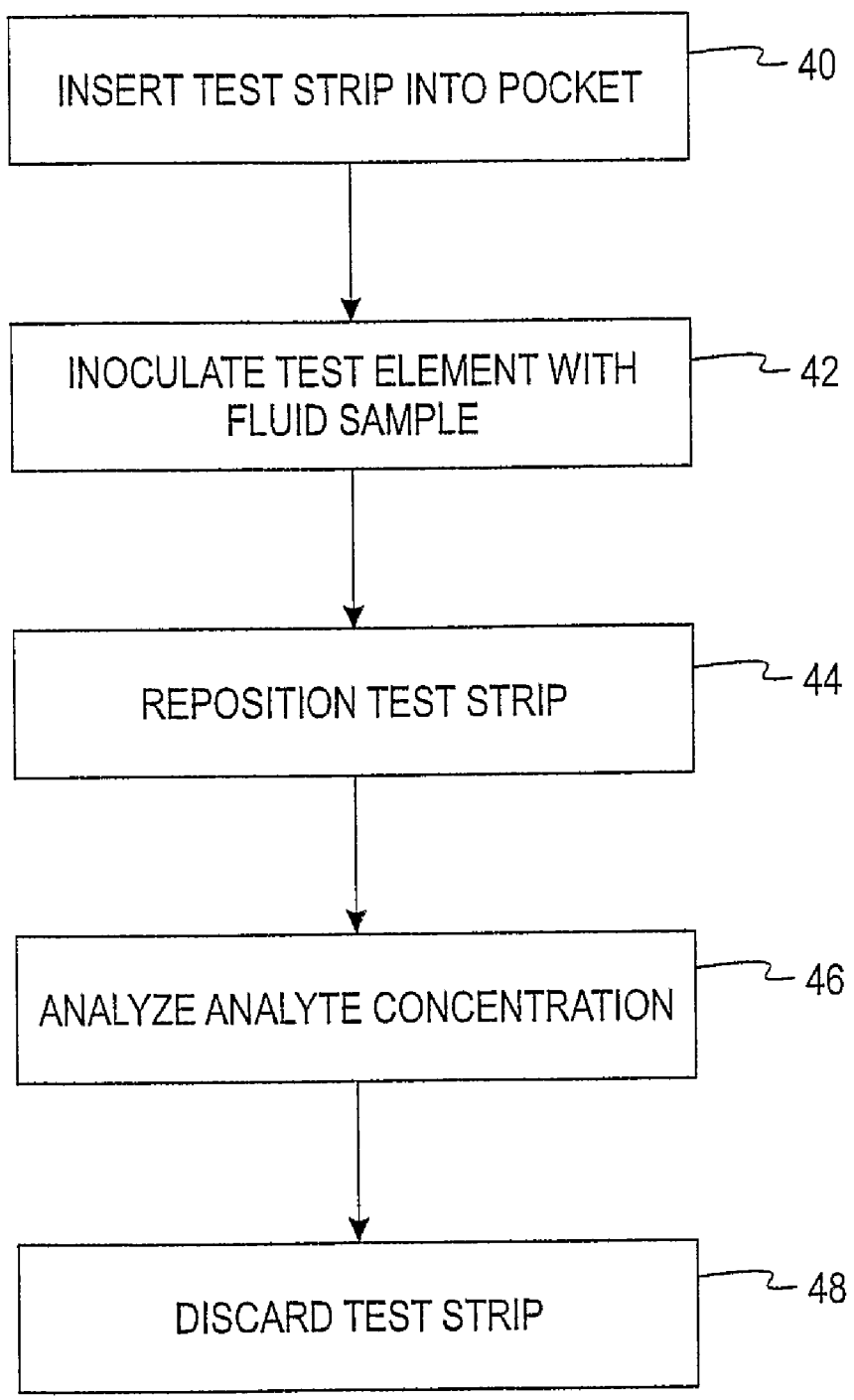
FIG. 5 is a flowchart illustrating a method for determining the concentration of an analyte in a fluid sample according to one embodiment of the present invention.

Referring now to FIG. 5, one method for analyzing an analyte in a fluid sample is shown. A test strip 22 (FIG. 1) is inserted onto a corresponding seating device—such as, for example, a pocket 30 (FIG. 2)—by a user at step 40. The user then may maneuver the test strip 22 by manipulating the meter 10. The user manipulates the meter 10 to maneuver the test strip 22 to inoculate the test element 24 with a fluid sample at step 42. At step 44, the user then repositions the inoculated test strip 22—by, for example, rotating the repositioning device 14 (FIG. 1)—to align the test element 24 with the read-head 12. The read-head 12 then analyzes the reaction between the analyte and the reactant and produces a signal that the meter 10 interprets to determine the concentration of the analyte at step 46. Finally, once the analyte concentration has been determined at step 46, the test strip 22 may be discarded at step 48.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

Alternative Embodiment A

A system for analyzing the concentration of an analyte in a fluid sample, the system comprising:
a test strip capable of being inoculated by the fluid sample, the test strip including a test element, the test element containing at least one reagent adapted to cause a reaction when brought into contact with the analyte in the fluid sample; and
a meter including a read-head, a repositioning device, and a display, the read-head being capable of producing a signal indicative of the reaction between the analyte and the at least one reagent, the display being capable of displaying the concentration of the analyte, the repositioning device being adapted to move the test strip from a loading position to a testing position, the testing position positioning the test element proximate to the read-head.

Alternative Embodiment B

The system according to embodiment A wherein the repositioning device is adapted to be moved by rotating the repositioning device about 90 degrees from the loading position to the testing position.

Alternative Embodiment C

The system according to embodiment A wherein the analyte is glucose.

Alternative Embodiment D

The system according to embodiment C wherein the fluid sample is a blood sample.

Alternative Embodiment E

The system according to embodiment A wherein the repositioning device includes a pocket being adapted to seat the test strip therein, the pocket being further adapted to allow the test strip to remain seated as the repositioning device moves from the loading position to the testing position.

Alternative Embodiment F

The system according to embodiment A wherein the repositioning device includes a post being adapted to seat the test strip thereon, the post being further adapted to allow the test strip to remain seated as the repositioning device pivots from the loading position to the testing position.

Alternative Embodiment G

The system according to embodiment F wherein the test strip includes an aperture extending through an end portion of the test strip, the end portion being opposite the test element.

Alternative Embodiment H

The system according to embodiment A wherein the test strip is a top-loaded test strip.

Alternative Embodiment I

The system according to embodiment A wherein the test strip is a semi-capillary test strip.

Alternative Embodiment J

The system according to embodiment A wherein the test strip is a capillary test strip.

Alternative Embodiment K

A meter for repositioning a test strip and determining the concentration of an analyte in a fluid sample, the meter comprising:
   a read-head capable of producing a signal indicative of a reaction between the analyte and at least one reagent; and
   a repositioning device including a test-strip-seating device, the repositioning device adapted to move the seated test strip from a loading position to a testing position, the testing position positioning a test element on the seated test strip proximate to the read-head,
   wherein the meter is adapted to maneuver the seated test strip when the meter is manipulated.

Alternative Embodiment L

The meter according to embodiment K wherein the repositioning device is adapted to be moved by rotating the repositioning device at least about 90 degrees.

Alternative Embodiment L1

The meter according to embodiment K wherein the repositioning device is adapted to be moved by rotating the repositioning device at least about 45 degrees.

Alternative Embodiment L2

The meter according to embodiment K wherein the repositioning device is adapted to be moved by rotating the repositioning device between at least about 45 degrees and about 180 degrees.

Alternative Embodiment M

The meter according to embodiment K wherein the repositioning device is adapted to be moved by rotating the repositioning device at least a full 360 degrees.

Alternative Embodiment N

The meter according to embodiment K wherein the test-strip-seating device is a pocket extending into the repositioning device, the pocket being adapted to allow an end portion of the test strip to be inserted.

Alternative Embodiment O

The meter according to embodiment K wherein the test-strip-seating device is a post extending from an outer surface of the repositioning device, the post being adapted to be inserted through an aperture in the end portion of the test strip.

Alternative Embodiment P

The meter according to embodiment K wherein the read-head is an optical read-head and the signal produced is indicative of a colorimetric reaction between the analyte and the at least one reagent.

Alternative Embodiment Q

The meter according to embodiment K wherein the repositioning device further includes a detector, the detector adapted to assist in determining the presence of a test strip, the repositioning device being adapted to automatically move the seated test strip from the loading position to the testing position upon the presence of the test strip.

Alternative Embodiment R

The meter according to embodiment K wherein the repositioning device is adapted to automatically move the seated test strip from the loading position to the testing position upon the presence of the test strip.

Alternative Process S

A method for analyzing the concentration of an analyte in a fluid sample, the method comprising the acts of:
   providing a meter including a read-head and a repositioning device, the repositioning device including a seating device located thereon;
   providing a test strip having a test element and an end portion removed spatially from the test element, the end portion of the test strip being adapted to correspond to the seating device;
   seating the test strip onto the corresponding seating device;
   inoculating the test element with the fluid sample, the fluid sample containing the analyte to be analyzed;
   repositioning the test strip, after inoculating the test element, the repositioning bringing the test element proximate to the read-head via the repositioning device; and
   determining the analyte concentration in the fluid sample.

Alternate Process T

The method according to Process R wherein the repositioning is performed by rotating the repositioning device.

Alternate Process U

The method according to Process T wherein the repositioning device is rotated about 90 degrees.

Alternate Process V

The method according to Process T wherein the repositioning device is adapted to rotate at least a full 360 degrees.

Alternate Process W

The method according to Process R wherein the seating device is a pocket extending into the repositioning device, the seating of the test strip being performed by inserting the end portion of the test strip into the pocket.

Alternate Process X

The method according to Process R wherein the seating device is a post extending from a surface of the repositioning device, the seating of the test strip being performed by inserting the post through an aperture in the end portion of the test strip.

Alternate Process Y

The method according to Process R wherein the repositioning the test strip is done automatically after the test strip is seated.

Alternative Process Z

A method for analyzing the concentration of an analyte in a fluid sample, the method comprising the acts of:

providing a meter including a read-head and a repositioning device, the repositioning device including a test-sensor receiving location;

providing a test strip having a test element and an end portion removed spatially from the test element, the end portion of the test strip being adapted to be located at the test-sensor receiving location;

placing the test strip at the test-sensor receiving location;

inoculating the test element with the fluid sample, the fluid sample containing the analyte to be analyzed;

repositioning the test strip, after inoculating the test element, the repositioning bringing the test element proximate to the read-head via the repositioning device; and determining the analyte concentration in the fluid sample.

Alternate Process AA

The method according to Process Z wherein the repositioning the test strip is done automatically after the test strip is placed.

Alternate Process BB

The method according to Process Z wherein the repositioning the test strip is done manually after the test strip is placed.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents and alternatives falling within the spirit and scope of the invention as defined by the appended claims.

The invention claimed is:

1. A system for analyzing the concentration of an analyte in a fluid sample, the system comprising:

a test strip configured to be inoculated by the fluid sample, the test strip including a test element, the test element containing at least one reagent adapted to cause a reaction when brought into contact with the analyte in the fluid sample; and a meter including a read-head, a repositioning device, and a display, the read-head being configured to produce a signal indicative of the reaction between the analyte and the at least one reagent, the display being configured to display the concentration of the analyte, the repositioning device being adapted to move the test strip from a loading position, whereat the test strip is inoculated by the fluid sample, to a testing position, whereat the test element is located proximate to the read-head such that the analyte concentration of the fluid sample can be determined from the test element by the read-head, the repositioning device being moved by rotating the repositioning device at least approximately 45 degrees from the loading position to the testing position.

2. The system according to claim 1, wherein the repositioning device is moved by rotating the repositioning device approximately 90 degrees from the loading position to the testing position.

3. The system according to claim 1, wherein the analyte is glucose.

4. The system according to claim 3, wherein the fluid sample is a blood sample.

5. A system for analyzing the concentration of an analyte in a fluid sample, the system comprising:

a test strip configured to be inoculated by the fluid sample, the test strip including a test element, the test element containing at least one reagent adapted to cause a reaction when brought into contact with the analyte in the fluid sample; and a meter including a read-head, a repositioning device, and a display, the read-head being configured to produce a signal indicative of the reaction between the analyte and the at least one reagent, the display being configured to display the concentration of the analyte, the repositioning device being adapted to move the test strip from a loading position, whereat the test strip is inoculated by the fluid sample, to a testing position, whereat the test element is located proximate to the read-head such that the analyte concentration of the fluid sample can be determined from the test element by the read-head, the repositioning device including a pocket adapted to seat the test strip therein, the pocket being further adapted to allow the test strip to remain seated as the repositioning device moves from the loading position to the testing position.

6. The system according to claim 1, wherein the repositioning device includes a post adapted to seat the test strip thereon, the post being further adapted to allow the test strip to remain seated as the repositioning device pivots from the loading position to the testing position.

7. The system according to claim 6, wherein the test strip includes an aperture extending through an end portion of the test strip, the end portion being opposite the test element, and the aperture being sized to fit on the post and thereby seat the test strip on the repositioning device.

8. The system according to claim 1, wherein the test strip is a top-loaded test strip.

9. The system according to claim 1, wherein the test strip is a semi-capillary test strip.

10. The system according to claim 1, wherein the test strip is a capillary test strip.

11. A meter for repositioning a test strip and determining the concentration of an analyte in a fluid sample, the meter comprising:

a read-head configured to produce a signal indicative of a reaction between the analyte and at least one reagent; and a repositioning device including a test-strip-seating device configured to attach the test strip to the repositioning device, the repositioning device being adapted to move the seated test strip from a loading position, whereat the test strip is inoculated by the fluid sample, to a testing position, whereat a test element on the seated test strip is located proximate to the read-head such that the analyte concentration of the fluid sample can be determined from the test element by the read-head, the repositioning device being moved by rotating the repositioning device at least approximately 45 degrees,
wherein the meter is adapted to maneuver the seated test strip when the meter is manipulated.

12. The meter according to claim 11, wherein the repositioning device is moved by rotating the repositioning device at least approximately 90 degrees.

13. The meter according to claim 11, wherein rotating the repositioning device rotates the test strip at least approximately 45 degrees about a common axis.

14. The meter according to claim 11, wherein the repositioning device is moved by rotating the repositioning device between at least approximately 45 degrees and approximately 180 degrees.

15. The meter according to claim 11, wherein the repositioning device is moved by rotating the repositioning device at least a full 360 degrees.

16. A meter for repositioning a test strip and determining the concentration of an analyte in a fluid sample, the meter comprising:
a read-head configured to produce a signal indicative of a reaction between the analyte and at least one reagent; and
a repositioning device including a pocket extending into the repositioning device and configured to attach the test strip to the repositioning device, the repositioning device being adapted to move the seated test strip from a loading position, whereat the test strip is inoculated by the fluid sample, to a testing position, whereat a test element on the seated test strip is located proximate to the read-head such that the analyte concentration of the fluid sample can be determined from the test element by the read-head, the pocket being adapted to seat therein an end portion of the test strip.

17. The meter according to claim 11, wherein the test-strip-seating device is a post extending from an outer surface of the repositioning device, the post being adapted to be inserted through an aperture in an end portion of the test strip.

18. The meter according to claim 11, wherein the read-head is an optical read-head and the signal produced is indicative of a colorimetric reaction between the analyte and the at least one reagent.

19. The meter according to claim 11, wherein the repositioning device further includes a detector, the detector adapted to assist in determining the presence of a test strip, the repositioning device being adapted to automatically move the seated test strip from the loading position to the testing position upon the presence of the test strip.

20. The meter according to claim 11, wherein the repositioning device is adapted to automatically move the seated test strip from the loading position to the testing position upon the presence of the test strip.

21. The system according to claim 1, wherein the repositioning device rotates about an axis to move the test element between the loading and testing positions, the axis of the repositioning device being aligned on a common plane with the location of the read-head and the location of the at least one reagent when the test element is in the testing position.

22. The system according to claim 21, wherein the meter further comprises an elongated housing, the axis of the repositioning device and the location of the at least one reagent when the test element is in the loading position being aligned along a common longitudinal plane of the housing.

23. The system according to claim 22, wherein the elongated housing has a longitudinal axis perpendicular to a lateral axis, the common longitudinal plane being parallel to the longitudinal axis.

24. The system according to claim 1, wherein the repositioning device is configured to automatically move the test element from the loading position to the testing position.

25. The system according to claim 24, wherein the repositioning device further comprises a detector adapted to detect the presence of the test element, the repositioning device being configured to automatically move the test element from the loading position to the testing position upon detection of the test element by the detector.

26. The system according to claim 1, wherein the read-head is an optical read-head which comprises at least one light source and a photodetector.

27. The system according to claim 1, wherein the meter further comprises a lancet operable to obtain a fluid sample.

28. The system according to claim 26, wherein the at least one light source comprises a light-emitting diode, and wherein the photodetector comprises a phototransistor.

29. The system according to claim 5, wherein the repositioning device rotates about an axis to thereby reposition the test element from the loading position to the testing position wherein the axis of the repositioning device is aligned on a common plane with the location of the read-head and the location of the at least one reagent when the test element is in the testing position, and wherein the repositioning device is configured to automatically move the test element from the loading position to the testing position.

30. The system according to claim 5, wherein the fluid sample is blood and the analyte is glucose.

31. The system according to claim 30, wherein the reaction between the glucose and the at least one reagent is a colorimetric reaction.

32. The system according to claim 5, wherein the repositioning device rotates at least 90 degrees to thereby reposition the test element from the loading position to the testing position.

33. The system according to claim 5, further comprising a lancet operable to obtain the fluid sample.

* * * * *